United States Patent [19]

Strickler

[11] Patent Number: 5,529,694

[45] Date of Patent: Jun. 25, 1996

[54] SOLID PHASE EXTRACTION APPARATUS AND METHOD OF USING SAME

[75] Inventor: Paul Strickler, Palms, S.C.

[73] Assignee: Environmental Express, Inc., Mt. Pleasant, S.C.

[21] Appl. No.: 332,942

[22] Filed: May 2, 1995

[51] Int. Cl.$^6$ .................................................. B01D 11/00
[52] U.S. Cl. .................... 210/634; 210/455; 210/460; 210/456; 210/416.1; 422/88; 422/89; 422/101
[58] Field of Search ................................. 210/634, 295, 210/263, 282, 416.1, 767, 321.84, 339, 455, 456, 474, 460, DIG. 6; 422/101, 88, 89

[56] References Cited

U.S. PATENT DOCUMENTS

| | | | |
|---|---|---|---|
| 2,728,459 | 12/1955 | Bender | 210/474 |
| 3,295,686 | 6/1968 | Krueger | 210/455 |
| 3,956,130 | 5/1976 | Cunningham et al. | 210/416.1 |
| 4,301,114 | 11/1981 | Rounbehler | 422/89 |
| 4,388,272 | 6/1983 | Gesteland | 422/88 |
| 5,240,680 | 8/1993 | Zuckermann et al. | 422/101 |
| 5,312,756 | 5/1994 | Jolly | 422/88 |

*Primary Examiner*—Ana Fortuna
*Attorney, Agent, or Firm*—B. Craig Killough

[57] ABSTRACT

An apparatus and method of determining trace levels of materials, such as oil and grease, which are present in liquids, such as water. The device and method allow the material to be extracted from the liquid by filtration, the material to be removed from the filter by a low boiling point solvent, and excess water to be removed from the solvent, by a single device. The apparatus is characterized by a tube having a manifold extending from the tube, with a valve which directs entry into the tubes which comprise the manifold. A crossover tube and an inner tube direct vacuum to allow a single vacuum connection to pull the liquid, and subsequently the solvent, through the apparatus. A drying cartridge is attached to a tube of the manifold to eliminate excess liquid from the solvent during the normal operation of the device.

9 Claims, 2 Drawing Sheets

SOLID PHASE EXTRACTION APPARATUS AND METHOD OF USING SAME

FIELD OF THE INVENTION

This invention relates to laboratory glassware and laboratory methods generally, and specifically relates to an apparatus which facilitates the determination of levels of trace amounts of materials which are in solution, and a method for using the apparatus.

BACKGROUND OF THE INVENTION

Levels of trace amounts of materials in solution with solvents, or suspended in liquids, having a relatively high boiling point are determined by filtering the materials from the higher boiling point solvents. In an additional step, the materials are placed into solution by means of a solvent having a lower boiling point. The lower boiling point solvent is then eliminated, and the quantity of material determined, such as by weighing the material.

Typically, levels of trace amounts of materials which are in solution in, or are suspended in, water are determined by this method. The materials are removed from the water by means of a filter. The filter may be selected as having an affinity for the materials to be removed. A solvent having a greater affinity for the materials than the filter, and having a relatively low boiling point, is used to remove the materials from the filter for collection and subsequent analysis or processing. The materials may be hydrocarbons, such as oil and grease, which are suspended in water.

More specifically, the sample is placed through the filter or other extraction medium, which extracts the material from the water. Typically, this has been done by applying a vacuum to a flask, and positioning a filter or extraction medium over the opening to the flask. The vacuum pulls the sample through the filter or extraction medium, and collects the material, while allowing the water to fall within the flask. The water is discarded and the filter or extraction medium is retained for further processing.

Such further processing requires manually handling the filtration apparatus that houses the filter or extraction medium, and again placing the filter or extraction medium adjacent to the opening of a flask. A solvent having a relatively low boiling point, and which is selected to extract the hydrocarbon from the filter or extraction medium, is used to extract the material from the filter. The solvent is passed through the filter and into the flask. The collected solvent, with the material in solution, is then available for further analysis or processing.

It is desirable to pass the solvent through an additional step to remove residual water. A drying material, such as sodium sulfate, may be used to dry the material. The drying material may be contained in a cartridge which is attached to the system.

In the prior art, the process described above is performed in three separate and distinct steps, each of which requires significant handling. A first flask must be set up before filtration or extraction of the material from the sample. A second flask is set up for the introduction of the solvent to the material. A third apparatus is set up to dry the solvent.

This process is time consuming, but further, requires undesired handling of the filter or extraction medium, and the extraction apparatus, which may introduce contamination into the process. Further, the method requires handling of solvents, which may be hazardous, especially in light of the use of solvents having low boiling points. Significant ventilation may be necessary for the solvents in the prior art method. This is especially true if the solvent is to be transported or poured, such as pouring the solvent through the drying material. Hazardous evaporation of the solvent continues to occur, resulting in the requirement of significant ventilation.

SUMMARY OF THE PRESENT INVENTION

The present invention provides a solid phase extraction apparatus and method of using same. This device and method eliminates excessive assembly and disassembly of the filter or extraction medium holder, thereby reducing the likelihood of introducing contamination into the process. The device and method substantially reduce the handling and evaporation of the solvent into the laboratory atmosphere. The apparatus and method allow the process described above to be performed with a single integrated apparatus, without multiple sets of flasks, and other laboratory glassware. The amount of time, and number of steps, required to perform the desired extraction is reduced substantially by the apparatus and method.

An upper tube is provided. A manifold extends from the upper tube. The manifold is comprised of a first lower tube and second lower tube. A valve is provided at a point of intersection of the upper tube and the first lower tube and second lower tube. The valve selectively directs a material introduced into the upper tube to either the first lower tube or the second lower tube. The valve may be used to terminate the flow from the upper tube.

A vacuum is applied to the first lower tube which allows a material to be drawn from the upper tube through the first lower tube for collection when the valve is directed accordingly. Through the use of a crossover tube which connects the first lower tube and the second lower tube, the application of the vacuum to the first lower tube also allows the material, upon redirection of the valve, to be pulled from the upper tube through an upper portion of the second lower tube, and into an inner tube which is positioned within a lower section of the second lower tube. A processing device, such as a drying cartridge may be positioned on a fitting, such as a luer fitting, on the lower portion of the inner tube. A sample may then be collected within a collection flask.

DETAILED DESCRIPTION OF THE PREFERRED EMBODIMENT

Figure 1:
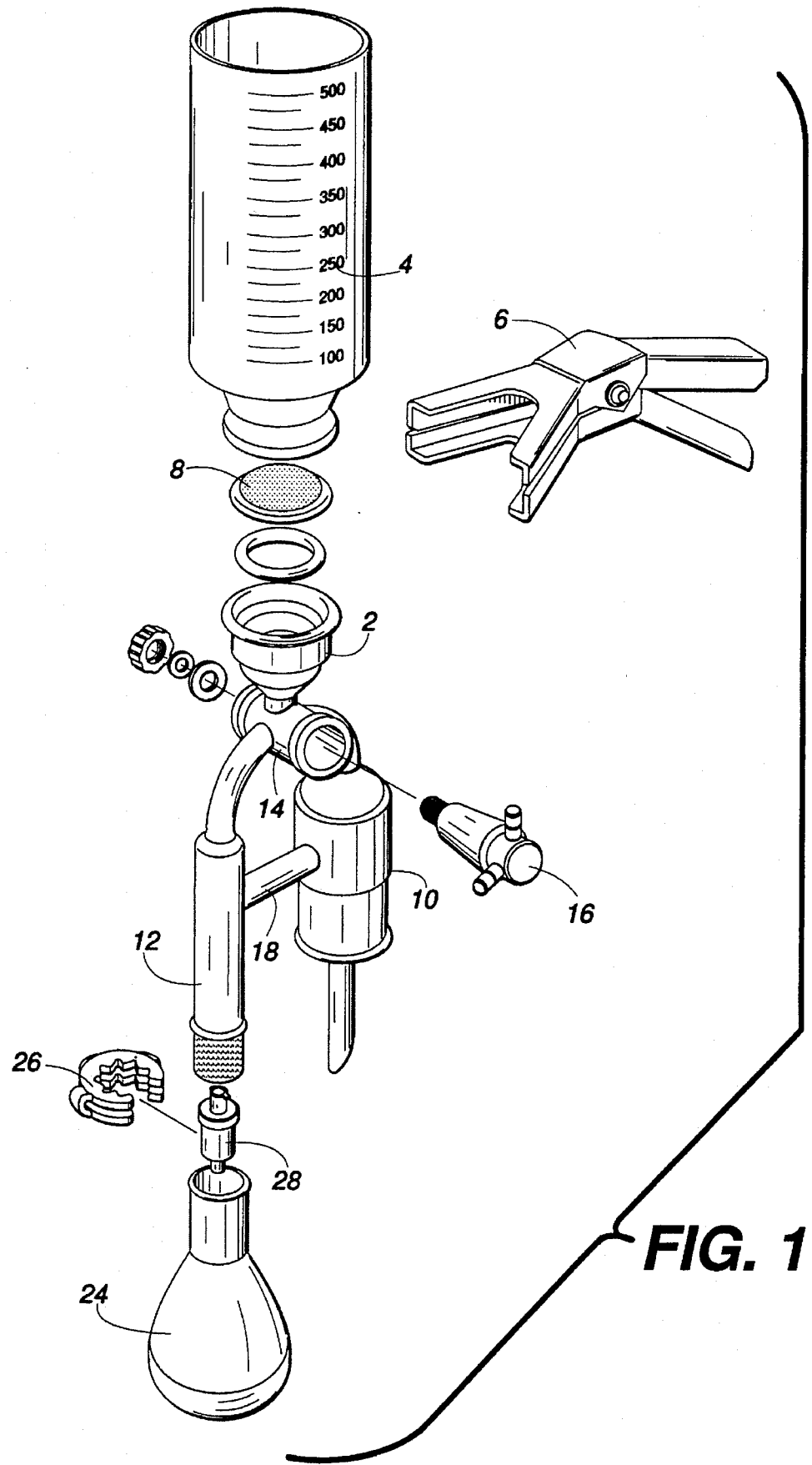
FIG. 1 is an exploded view of the solid phase extraction apparatus.
Figure 2:
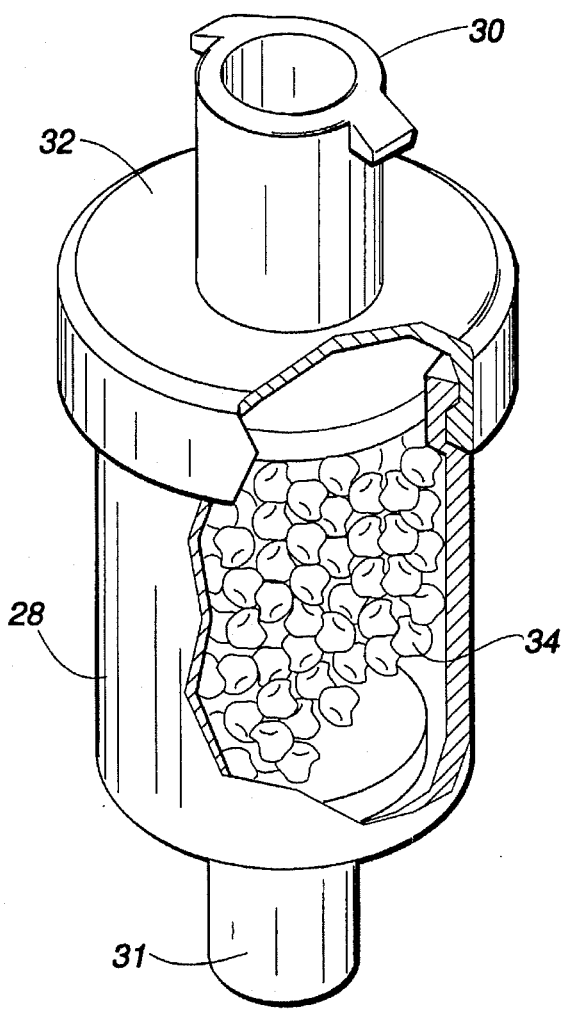
FIG. 2 is an enlarged isolation of the drying cartridge which is partially cut away to reveal the contents.
Figure 3:
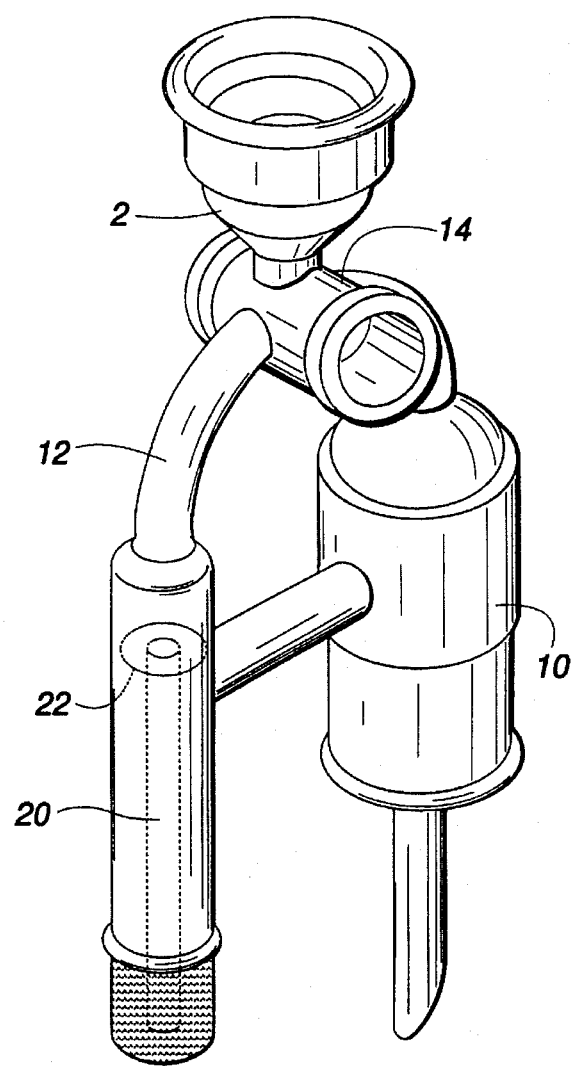
FIG. 3 is an enlarged view of the solid phase extraction apparatus.

Referring now to the drawing figures, the solid phase extraction apparatus is shown in FIG. 1. As shown in the preferred embodiment, the upper tube 2 may comprise an opening which will accept a funnel 4. The funnel may be mounted to the upper tube by means of a clamp 6, which will allow an air tight seal between the funnel and the upper tube. A filter 8 or extraction medium is positioned within the upper tube. The filter or extraction medium is chosen according to the material which is to be extracted from the sample.

A manifold extends from the upper tube. The manifold is comprised of a first lower tube 10 and a second lower tube 12. The first upper tube, the first lower tube, and the second lower tube each communicate with each other, and have a common intersection, or a junction 14.

A valve 16 is located at the junction. A housing may be provided for the valve. A valve which is commonly known as a stopcock may be used. The stopcock may be a 120° stopcock, which allows a material which enters the upper tube to be selectively directed to the first lower tube or the second lower tube.

The first lower tube may be provided with a fitting, such as a female 40–35 glass joint, which allows an air tight mounting to a container. The container may be mounted to a vacuum manifold having a 40–35 male glass joint. An extension may extend from the first lower tube.

A crossover tube 18 extends from the first lower tube along the length of the first lower, and connects with the second lower tube along the length of the second lower tube. The crossover tube allows air pressure or vacuum communication between the first lower tube and the second tube.

The second lower tube has an inner tube 20 positioned within an interior of the second lower tube. This inner tube may have a connecting fitting at the lower end of the inner tube, such as a male luer fitting, or other appropriate connection that facilitates the connection of a drying device. At, or near, the top of the inner tube is a flange 22 which divides an upper portion of the second lower tube from a lower portion of the second lower tube. The flange, or ring seal, allows the inner tube to communicate with the upper portion of the second lower tube. The flange is positioned above the point where the crossover tube joins the second lower tube, so that the inner tube has a point of exit which is below the crossover tube. The crossover tube connects to and communicates directly with the lower portion of the second lower tube. Accordingly, material is pulled from the upper portion of the second lower tube through the inner tube, and not through the lower portion of the second lower tube.

The second lower tube may be constructed for air tight mounting, such as a 20–25 male glass joint, to a container, such as a collection flask 24, by means of a 25–20 female glass joint. A clamp 26 may be provided for joining the collection flask for the lower end of the second lower tube.

A drying cartridge 28 is positioned to the end of the inner tube. The drying cartridge has an entrance and an exit, with a drying material present within the cartridge. The entrance of the drying cartridge may be a female luer fitting 30 that attaches to the male luer 31 fitting of the inner tube. The exit of the drying cartridge may be a male luer fitting which allows additional luer fittings, such as a series of drying cartridges, to be placed entrance to exit. Sodium sulfate may be used as a drying material to remove water from the composition which passes through the drying cartridge. The drying cartridge is attached to the lower portion of the inner tube.

The housing 32 may be constructed of polypropylene. Anhydrous sodium sulfate crystals 34 are packed in the cartridge housing between high density polyethylene frits 36.

In use, a filter 8 is positioned within the upper tube 2. A funnel 4 or similar container is connected to the upper tube. The first lower tube 10 is fitted in an air tight manner with a container, and the container is attached to a manifold through which a vacuum source is applied. The drying cartridge 28 is present on the end of the inner tube, and a collection flask 24 is fitted to the second lower tube.

A vacuum is applied to the first lower tube by means of the vacuum source. The valve 16 is positioned to cause material passing through the junction to be directed to the first lower tube. A sample, which will typically be water having a hydrocarbon material present, is measured and is placed in the funnel. Alternatively, the sample may be measured within the funnel, and the solvent soaking steps maybe regulated with the valve in a "neutral" position which will prevent, or control the rate of flow of, the material passing into the manifold.

The vacuum causes the material to be pulled through the filter or extraction medium, and into the container which is positioned underneath the first lower tube. A solvent is measured and placed with in the funnel, or is measured within the funnel. The valve is then moved from a neutral position to a position which will cause the material to be drawn from the funnel through the filter, the valve, the upper portion of the second lower tube, the inner tube and the drying cartridge, and into the collection flask.

The positioning of the crossover tube 18 allows the vacuum which is applied to the first lower tube to be used for pulling the solvent through the second lower tube, the inner tube and into the collection flask. The use of the flange which separates the upper portion of the second lower tube from the lower portion of the second lower tube causes the vacuum to be directed through the collection flask, thereby pulling the liquid material through the inner tube and the drying cartridge and into the collection flask. The use of air tight fittings for mounting of the container to the first lower tube, and the mounting of the collection flask to the second lower tube, allows a single vacuum source to effectively pull the liquids through the filter and into the flask or container as desired, by appropriately directing the valve.

The drying cartridge completes the processing by the apparatus. The filter and the apparatus may have residual water after the hydrocarbon material is filtered from the water and the sample. It is desirable to eliminate this residual water, which has a relatively high boiling point, to leave only the material to be analyzed and the low boiling point solvent present within the collection flask. The drying cartridge has a material present therein that eliminates water from the material which passes through the cartridge. Sodium sulfate may be used as a drying agent for the purpose of eliminating residual water for most applications.

A common use for the device is for the analysis of trace amounts of oil and grease, which are comprised of animal and petroleum hydrocarbons, in water. A goal of such analysis is to remove the oil or grease from the water, and to place the oil or grease in solution by use of a solvent which has a low boiling point and which has an affinity for oil and grease. The solvent is then eliminated, so that the levels of oil or grease which are present within the volume of the sample may be determined.

In such an application, a predetermined volume of a water sample is placed within the funnel or similar container, according to the method above. An appropriate filter is used to extract the oil and grease from the water, and the vacuum is applied to the device. The sample is directed by the vacuum through the valve and the first lower tube and into a container. A volume of hexane is introduced. The valve is then repositioned to direct the hexane through the second lower tube, by means of the vacuum which is applied to the first lower tube. The hexane has an affinity for oil and grease, and will extract the oil and grease from the filter and direct it, in solution, into the collection flask.

As the hexane, with oil and grease, pass through the second lower tube and exit the inner tube, residual water is removed from the composition by means of sodium sulfate present within the drying cartridge.

Hexane, which has a low boiling point, may easily be eliminated from the collection flask, and the amount of oil and grease which is present within a collection flask may be determined by weighing the flask. The amount of oil and grease which are present in the sample, and accordingly, the concentration of oil and grease which are within the sample, may then easily be calculated.

Following the determination of the oil and grease content in the collection flask, solvent such as n-Hexane may be added to the collection flask and the oil and grease brought back into solution. Once in solution, silica gel may be added to the solution. The silica gel retains the animal fats and greases, and leaves the remaining total petroleum hydrocarbons in solution.

The drying cartridge is then removed, and a second collection flask is attached to the bottom of the second lower tube in the same manner as the first collection flask. The impregnated filter or filter media is removed from beneath the upper tube, and replaced with an unimpregnated filter or media.

Vacuum is applied with the valve directing or controlling flow into the second lower tube. The silica gel treated solution is then placed in to the upper tube, and the silica gel in the silica gel treated solution is retained in, or on, said unimpregnated filter or filter media, thereby separating the silica gel with the animal fats from the total petroleum hydrocarbons in solution.

The vacuum or air pressure causes the total petroleum hydrocarbon solution to enter the inner tube, and to be deposited into the second collection flask. The second collection flask may then be removed, and the total petroleum hydrocarbon content of the sample determined.

What is claimed is:

1. A solid phase extraction apparatus, comprising:
   a. an upper tube having a filter or extraction medium disposed at an upper section of the tube;
   b. a manifold extending from said upper tube, and having a first lower tube which communicates with said upper tube and a second lower tube which communicates with said upper tube;
   c. a valve which is positioned between said upper tube, said first lower tube and said second lower tube, and which receives a flow of liquid material from said upper tube and selectively directs the flow of liquid material between said first lower tube and said second lower tube;
   d. a crossover tube which connects said first lower tube with said second lower tube;
   e. an inner tube which is positioned within a lower portion of said second lower tube, said inner tube having means for separating an upper portion of said second lower tube from a lower portion of said second lower tube, wherein said crossover tube joins said second lower tube along said lower portion of said second lower tube, and wherein said upper portion of said second lower tube communicates with said crossover tube and said first lower tube by means of said inner tube; and
   f. drying cartridge means which communicates with an opening in a lower end of said inner tube.

2. A solid phase extraction apparatus as described in claim 1, wherein an upper end of said inner tube opens into said upper portion of said second lower tube, and wherein said means for separating an upper portion of said second lower tube from said lower portion of said second lower tube is a flange which extends from said upper end of said inner tube to an inner wall of said second lower tube.

3. A solid phase extraction apparatus as described in claim 2, wherein said drying cartridge means is attached to said inner tube.

4. A solid phase extraction apparatus as described in claim 3, further comprising a collection flask which is positioned below and attached to said second lower tube by sealing means, and wherein said drying cartridge communicates with said collection flask, and wherein said collection flask communicates with said first lower tube through said crossover tube, and said collection flask communicates with said upper portion of said second lower tube through said inner tube.

5. A solid phase extraction apparatus as described in claim 2, further comprising a collection flask which is positioned below and attached to said second lower tube by sealing means, and wherein said drying cartridge communicates with said collection flask, and wherein said collection flask communicates with said first lower tube through said crossover tube, and said collection flask communicates with said upper portion of said second lower tube through said inner tube.

6. A solid phase extraction apparatus as described in claim 1, wherein said drying cartridge means is attached to said inner tube.

7. A solid phase extraction apparatus as described in claim 6, further comprising a collection flask which is positioned below and attached to said second lower tube by sealing means, and wherein said drying cartridge communicates with said collection flask, and wherein said collection flask communicates with said first lower tube through said crossover tube, and said collection flask communicates with said upper portion of said second lower tube through said inner tube.

8. A solid phase extraction apparatus as described in claim 1, further comprising a collection flask which is positioned below and attached to said second lower tube by sealing means, and wherein said drying cartridge communicates with said collection flask, and wherein said collection flask communicates with said first lower tube through said crossover tube, and said collection flask communicates with said upper portion of said second lower tube through said inner tube.

9. A method of using a solid phase extraction apparatus comprising the steps of:
   a. taking an apparatus comprising an upper tube, a manifold comprising a first lower tube which communicates with said upper tube and a second lower tube which communicates with said upper tube, a valve which is positioned between said upper tube, said first lower tube and said second lower tube and which receives a liquid from said upper tube and selectively directs the liquid material between said first lower tube and said second lower tube; said second lower tube having an upper portion and a lower portion, and an inner tube in said lower portion communication at its lower end with a drying cartridge; a crossover pipe communicating the first lower pipe with the lower portion of the second lower pipe;
   b. directing liquid through a filter provided in said upper tube;
   c. applying vacuum to the apparatus through said first lower tube;
   d. drawing the liquid material through said upper tube, said filter, said valve, and said first lower tube by means of the vacuum;
   e. repositioning said valve;

f. introducing a solvent into said filter;
g. drawing said solvent through said filter, said upper tube, said valve, said upper portion of said second lower tube, said inner tube present in said lower portion of said second lower tube, and said drying cartridge, by means of the vacuum which is applied to said apparatus through said first lower tube; and
h. collecting said solvent.

* * * * *